United States Patent
Schnaars et al.

(10) Patent No.: US 9,427,546 B2
(45) Date of Patent: Aug. 30, 2016

(54) CONNECTING UNIT FOR COMPONENTS IN A BREATHING SYSTEM

(75) Inventors: Henryk Schnaars, Lübeck (DE); Dirk Stefan Reichert, Lübeck (DE)

(73) Assignee: DRAEGERWERK AG & CO. KGAA, Luebeck (DE)

( * ) Notice: Subject to any disclaimer, the term of this patent is extended or adjusted under 35 U.S.C. 154(b) by 190 days.

(21) Appl. No.: 13/067,057

(22) Filed: May 5, 2011

(65) Prior Publication Data

US 2011/0284000 A1   Nov. 24, 2011

(30) Foreign Application Priority Data

May 20, 2010   (DE) .................. 10 2010 022 205

(51) Int. Cl.
    *A61M 16/08*    (2006.01)
    *A61M 39/10*    (2006.01)

(52) U.S. Cl.
    CPC ......... *A61M 16/0816* (2013.01); *A61M 39/10* (2013.01)

(58) Field of Classification Search
    CPC ... F16L 33/34; A61M 16/0816; A61M 39/10
    USPC ...... 285/141.1, 139.2, 213, 215, 216, 334.1, 285/347
    See application file for complete search history.

(56) References Cited

U.S. PATENT DOCUMENTS

| | | | | |
|---|---|---|---|---|
| 2,454,707 A | * | 11/1948 | Meyers et al. ................... | 57/122 |
| 2,670,976 A | * | 3/1954 | Owen ........................... | 277/606 |
| 4,072,245 A | * | 2/1978 | Sloan, Jr. ...................... | 220/295 |
| 5,138,117 A | * | 8/1992 | Oikawa et al. ............ | 174/152 G |
| 5,435,605 A | * | 7/1995 | Koumatsu et al. ........... | 285/110 |
| 5,692,858 A | * | 12/1997 | Vaughan ........................ | 405/43 |
| 6,446,686 B2 | * | 9/2002 | Pozgainer et al. ............ | 141/350 |
| 6,805,119 B2 | | 10/2004 | Hoffmann et al. | |
| 7,891,709 B2 | * | 2/2011 | Choi ............................. | 285/215 |
| 2001/0037840 A1 | | 11/2001 | Pozgainer et al. | |

OTHER PUBLICATIONS

Niemann, G., "Maschinenelemente, Band I, Konstruktion und Berechnung von Verbindung, Lagern, Wellen", 1981, p. 342, Table 16/8, Springer-Verlag, Berlin, Heidelberg, Germany.

* cited by examiner

*Primary Examiner* — David E Bochna
*Assistant Examiner* — James Linford
(74) *Attorney, Agent, or Firm* — Walter Ottesen, P.A.

(57) ABSTRACT

A connecting unit for fixing components in a breathing system includes a plug adapter (2) having a sealing element (1). The sealing element (1) has a first peripheral fastening thickening (4), a second fastening thickening (5) arranged at a distance to the first fastening thickening (4), as well as an undercut (7) between the fastening thickenings (4, 5). The second fastening thickening (5) has an outer lead-in chamfer (6) for a receiving bore into which the plug adapter (2) along with the sealing ring (1) are inserted.

5 Claims, 2 Drawing Sheets

CONNECTING UNIT FOR COMPONENTS IN A BREATHING SYSTEM

CROSS REFERENCE TO RELATED APPLICATION

This application claims priority of German patent application no. 10 2010 022 205.4, filed May 20, 2010, the entire contents of which is incorporated herein by reference.

FIELD OF THE INVENTION

The invention relates to a connecting unit for components in a breathing system.

BACKGROUND OF THE INVENTION

A breathing system with a circulation of breathing air is known from U.S. Pat. No. 6,805,119 B2. The known breathing system has a layered structure and includes a breathing gas block, a valve plate and a cover. The breathing gas block is provided with breathing gas connections via which the patient is supplied with breathing gas. Partition walls are located within the breathing gas block through which breathing gas channels are formed within the breathing gas block. The valve plate has directional valves which are located on the upper side of the valve plate and with which the direction of the breathing gas flow can be controlled. The cover is located above the valve plate. The cover forms the upper end of the breathing system and is connected to the breathing gas block via a quick acting closure system. In components which are fixed on the metallic valve plate, it is important that, on the one hand, easy cleaning is possible at the connection joints and that components can be exchanged without the use of tools by the service. On the other hand, the fixation of the components must be so stable that the connection joints cannot be accidentally disengaged.

SUMMARY OF THE INVENTION

It is an object of the invention to provide a connecting unit for components in a breathing system which is simple to manufacture and has good performance characteristics.

The connecting unit of the invention is for a component in a breathing system. The connecting unit includes: a plug adapter; a sealing element arranged on the plug adapter and configured to peripherally seal the plug adapter on a receiving bore; the sealing element being made of elastic, deformable material and having a first peripheral fastening thickening and a second fastening thickening arranged at a distance from the first fastening thickening; the sealing element further including an undercut arranged between the first and second fastening thickenings and configured as a deformation zone; and, the second fastening thickening of the sealing element having an outer lead-in chamfer configured for the receiving bore.

The connecting unit for the fixing of components in a breathing system is made up of the combination of a plug adapter with a sealing ring. The sealing ring is vulcanized onto the plug adapter or is otherwise permanently connected to the plug adapter. Thus, bacteria are prevented from settling between the sealing ring and the plug adapter. The sealing ring is made of an elastic, deformable material, for example, silicon, rubber or a thermoplastic plastic. The sealing ring has a first peripheral fastening thickening and a second fastening thickening arranged at a distance to the first fastening thickening as well as an undercut between the fastening thickenings as a deformation zone. The second fastening thickening additionally has an outer lead-in chamfer with which the second fastening thickening can be inserted into a receiving bore together with the adapter plug. The receiving bore is preferably located on an assembly plate on which the component is to be fastened. The assembly plate can be part of the breathing system or is part of a breathing unit. The connecting unit can be used universally inside the breathing unit and is not limited to the use in breathing-gas-supplying areas of a breathing system.

When the lead-in chamfer touches the edge of the receiving bore during the insertion of the plug adapter into the receiving bore, the second fastening thickening is deformed in the direction of the undercut, which is located between the two fastening thickenings, and the second fastening thickening is pushed through on the inner side of the receiving bore until it snaps out on the opposite side. When the plug adapter is fully inserted the fastening thickenings are on the top and the bottom side, respectively, of the receiving bore and, through the form fit, perform a holding function of the plug adapter inside the receiving bore as well as a sealing function by means of which liquids, particles, or bacteria are prevented from penetrating into the sealing area. Thus, a quasi radial sealing between the two parts is achieved, without having any hard-to-access dead spots typical of radial seals, such as O-ring grooves, in which bacteria can settle and where it is difficult or impossible for disinfectants to reach.

The undercut between the fastening thickenings is configured in such a manner that beginning with a first section it has parallel, distanced wall surfaces, and in an adjacent second section, a trapezoidally-shaped cross-sectional contour. A half circle, an oval, and/or an elliptical shape are alternatives to the trapezoidally-shaped cross-sectional contour. The parallel, spaced wall surfaces of the undercut rest against the outside of the receiving bore and function as the liquid and particle seal.

Advantageously, the first fastening thickening in the first section of the undercut has at least three times the material thickness of the second fastening thickening. As a result of the greater material thickness in the region of the first fastening thickening, the first fastening thickening acts as a stop so that the plug adapter cannot slide out when being inserted into the receiving bore. The first fastening thickening can be deformed on the other side to such an extent that the second fastening thickening on the opposing side of the receiving bore can snap out of the receiving bore. Because of the design of the second fastening thickening in dependence on the hardness of the elastomer, the holding function can be adjusted in such a way that the plug adapter can be removed with ease, with difficulty or only by destroying the elastomer.

A further stiffening of the first fastening thickening is achieved in that the first fastening thickening has a larger outer diameter than the second fastening thickening.

The connecting unit is suited for the fixation of pneumatic elements such as valves or switching elements inside the breathing system which must be serviced or replaced by technical personnel on location. Because of the design of the sealing ring, which serves to fix the plug adapter inside the receiving bore, a simple plug-in assembly is achieved, and the sealing thickenings of the sealing ring seal both sides of the receiving bore against the penetration of liquids and bacteria. Since the sealing ring is fixed on both sides of the receiving bore some self centering of the plug adapter results inside the receiving bore, because upon deflection, for example, by external forces, the plug adapter will return to its initial position as a result of the elasticity of the sealing ring. The space between the two fastening thickenings must be dimensioned such that when pushing the second fastening thickening through the bore of the assembly plate, the displaced material volume of the second fastening thickening is accommodated.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
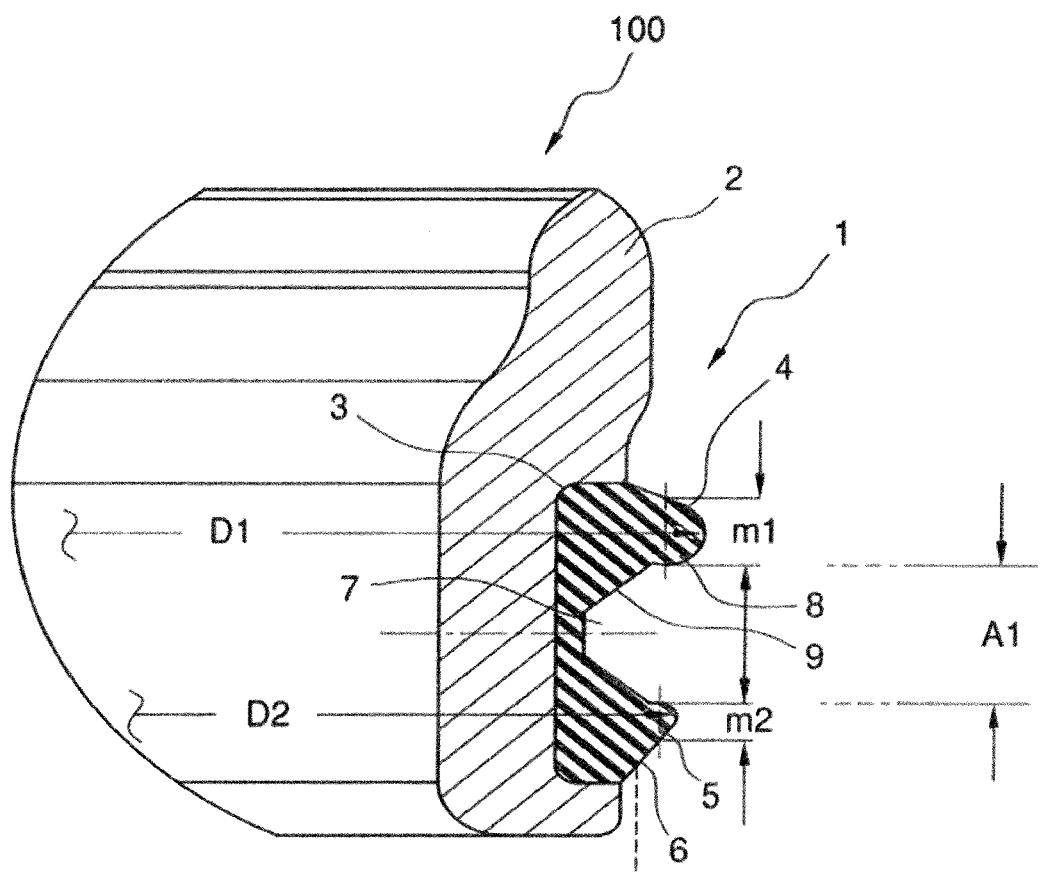
FIG. 1 shows a connecting unit according to the invention.

FIG. 1 is a sectional view of a connecting unit 100 according to the invention, which includes a sealing element 1 on a plug adapter 2. The sealing element 1 is made up of an elastomer and is vulcanized in a groove 3 on the plug adapter The sealing element 1 has a first peripheral fastening thickening 4 and, at a distance thereto, a second fastening thickening 5 having an outer lead-in chamfer 6 and an undercut 7 between the fastening thickenings 4 and 5 as a deformation zone for the second fastening thickening 5.

The first fastening thickening 4 has a greater outer diameter $D_1$ than the second fastening thickening 5 having the outer diameter $D_2$. The undercut 7 between the fastening thickenings 4 and 5 begins in a first section 8 having parallel, spaced wall surfaces and ends in a second section 9 having a trapezoidally-shaped cross-sectional contour.

In the area of the first section 8, the material thickness $m_1$ of the first fastening thickening 4 is at least three times greater than the material thickness $m_2$ of the second fastening thickening 5. The clear distance between the fastening thickenings (4, 5) in the region of the first section 8 is $A_1$.

Figure 2:
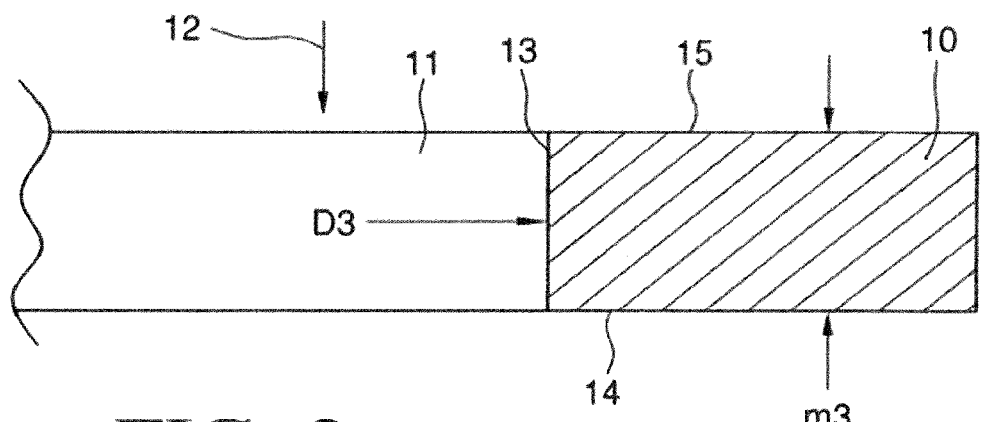
FIG. 2 shows a receiving bore for the connecting unit of FIG. 1.

FIG. 2 is a sectional view assembly plate 10 having a receiving bore 11 for fixation of the connecting unit 100 of FIG. 1. The inner diameter $D_3$ of the receiving bore 11 is designed in such a manner that it is approximately about 8% smaller than the outer diameter $D_2$ of the second fastening thickening 5. The material thickness $m_3$ of the assembly plate 10 is approximately 10% larger than the clear distance $A_1$ in the first section 8 of the undercut 7.

The insertion of the plug adapter 2 together with the sealing ring 1 into the receiving bore 11 of the assembly plate 10 occurs along the arrow 12. In this way, the first end of the inner surface 13 of the receiving bore 11 initially comes into contact with the lead-in chamfer 6, and the second fastening thickening 5 is deformed in the direction of the undercut 7. With a further movement of the plug adapter 2 in the direction of arrow 12, the deformed second fastening thickening 5 slides on the inner surface 13 until it reaches the second end of the inner surface 13 at the bottom side 14 of the assembly plate 10 and snaps out of the receiving bore 11. Thereafter, the first fastening thickening 4 rests against the upper side 15 of the assembly plate 10 and the second fastening thickening 5 is on the bottom side 14. Because of the elasticity of the material of the sealing element 1, the receiving bore 11 is sealed on the upper side 15 by means of the first fastening thickening 4, and the seal on the bottom side 14 of the assembly plate 10 is achieved by the second fastening thickening 5.

Figure 3:
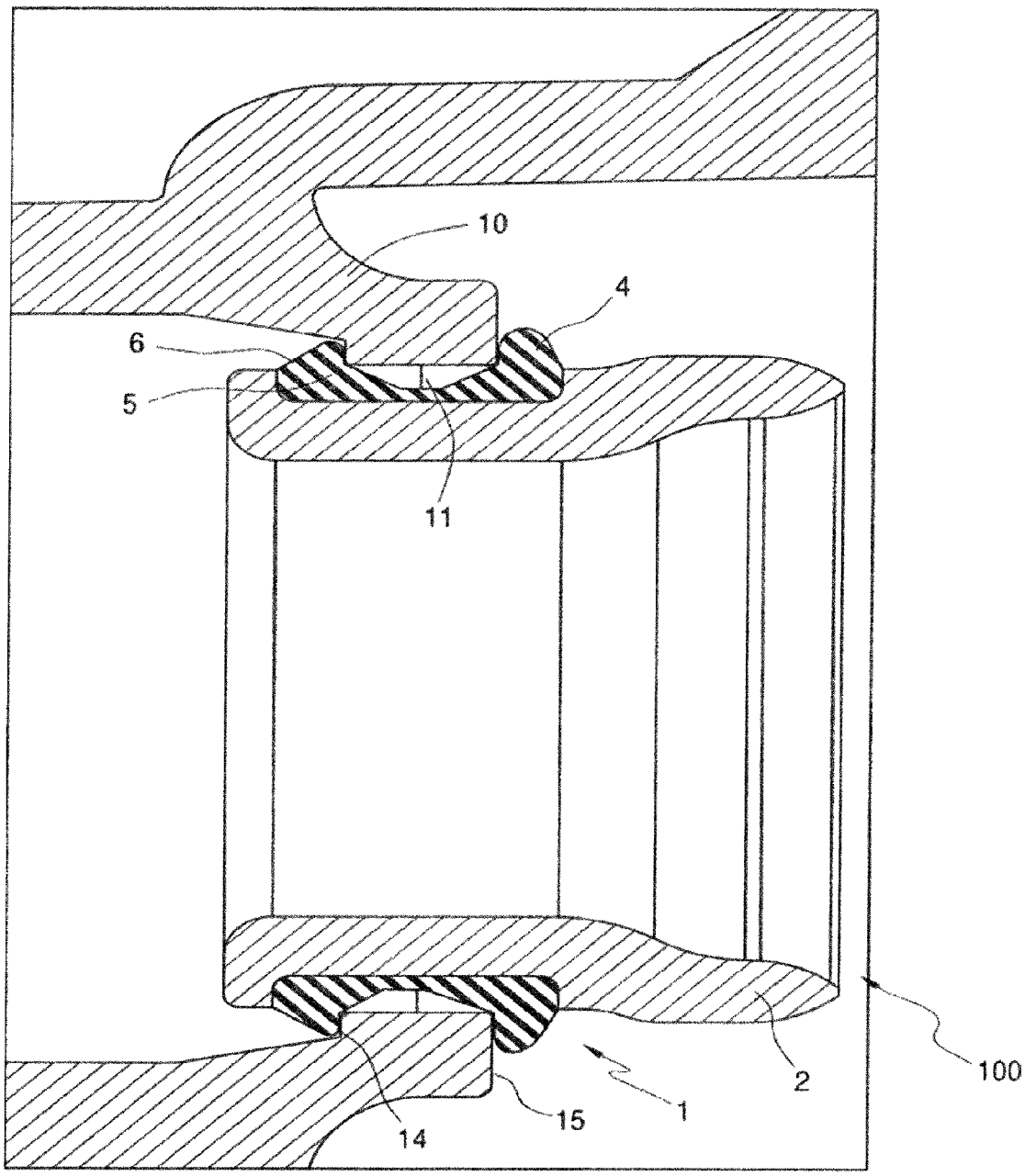
FIG. 3 shows the connecting unit of FIG. 1 in the receiving bore.

FIG. 3 shows the connecting unit 100 completely inserted into the receiving bore 11 of the assembly plate 10. The same components are referenced by the same reference numerals as in FIGS. 1 and 2. The fastening thickenings (4, 5) are located at respective ends of the receiving bore 11 and effect the self centering of the plug adapter 2 inside the assembly plate 10.

It is understood that the foregoing description is that of the preferred embodiments of the invention and that various changes and modifications may be made thereto without departing from the spirit and scope of the invention as defined in the appended claims.

REFERENCE NUMERALS

1 Sealing element
2 Plug adapter
3 Groove
4 First fastening thickening
5 Second fastening thickening
6 Lead-in chamfer
7 Undercut
8 First section
9 Second section
10 Assembly plate
11 Receiving bore
12 Arrow
13 Inner surface
14 Bottom side
15 Upper side
100 Connecting unit

What is claimed is:

1. An assembly plate for a breathing system, said assembly plate comprising:

a connecting unit including a plug adapter;

a sealing element arranged in a groove of said plug adapter and being configured to peripherally seal said plug adapter on a receiving bore of said assembly plate;

said sealing element being made of elastic, deformable material and having a first peripheral fastening thickening and a second peripheral fastening thickening arranged at a distance from said first fastening thickening;

said sealing element further including an undercut arranged between the first and second fastening thickenings and configured as a deformation zone;

said second fastening thickening of said sealing element having an outer lead-in chamfer configured for said receiving bore;

said undercut being insertable into said receiving bore;

said undercut having a first section having mutually parallel spaced wall surfaces and a second section having a trapezoidally-shaped cross-sectional contour extending between said parallel spaced wall surfaces;

said receiving bore having a first end, a second end, and an inner surface that extends from the first end to the second end;

said receiving bore being positioned between and abutting the parallel spaced wall surfaces and the inner surface extending over the trapezoidally-shaped cross-sectional contour and forming a void between the inner surface and a surface of the trapezoidally-shaped cross-sectional contour;

said undercut and said inner surface forming said deformation zone; and, said plug adapter being self-centering in said receiving bore, wherein said receiving bore has a material thickness ($m_3$); and, wherein said first and second fastening thickenings define an inner distance ($A_1$) in said first section which is less than said material thickness ($m_3$).

2. The connecting unit of claim 1, wherein:

said first fastening thickening has a material thickness ($m_1$);

said second fastening thickening has a material thickness ($m_2$); and, said material thickness ($m_1$) of said first fastening thickening is at least three times greater than said material thickness ($m_2$) of said second fastening thickening.

3. The connecting unit of claim 1, wherein:

said first fastening thickening has an outer diameter ($D_1$);

said second fastening thickening has an outer diameter ($D_2$); and, said outer diameter ($D_1$) of said first fastening thickening is greater than said outer diameter ($D_2$) of said second fastening thickening.

4. The connecting unit of claim 1, wherein said sealing element is affixed to said plug adapter such that growth of bacteria in said groove is prevented.

5. The connecting unit of claim 4, wherein said sealing element is vulcanized into said plug adapter.

* * * * *